United States Patent [19]

Saito et al.

[11] 4,398,043

[45] Aug. 9, 1983

[54] PROCESS FOR PREPARING CYCLOPENTENOLONES

[75] Inventors: Kenji Saito, Toyonaka; Yukihisa Takisawa; Hiroshi Yamachika, both of Ibaraki, all of Japan

[73] Assignee: Sumitomo Chemical Company, Limited, Osaka, Japan

[21] Appl. No.: 324,135

[22] Filed: Nov. 23, 1981

[30] Foreign Application Priority Data

Dec. 10, 1980 [JP] Japan .................................. 55-175144
Dec. 16, 1980 [JP] Japan .................................. 55-178326

[51] Int. Cl.³ ............................................. C07C 45/59
[52] U.S. Cl. ........................................ 568/322; 568/361
[58] Field of Search ................ 568/310, 322, 341, 361

[56] References Cited

U.S. PATENT DOCUMENTS 3,932,510 1/1976 Muller ................................ 568/341
3,981,920 9/1976 Buchi ................................. 568/379

OTHER PUBLICATIONS

Scettri et al., Tetrahedron, vol. 35, pp. 135-138, (1979).
Piancatelli et al., Tetrahedron, 34, pp. 2775-2778, (1978).
Piancatelli et al., Tetrahedron Letters No. 39, pp. 3555-3558, (1976).

Primary Examiner—James H. Reamer
Attorney, Agent, or Firm—Birch, Stewart, Kolasch & Birch

[57] ABSTRACT

A process for preparing cyclopentenolones of the formula:

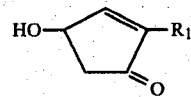

wherein $R_1$ is a straight, branched or cyclic alkyl group having not more than 6 carbon atoms, a straight, branched or cyclic alkenyl group having not more than 6 carbon atoms, a straight or branched alkynyl group having not more than 6 carbon atoms or a group of the formula:

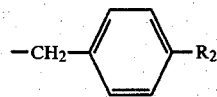

wherein $R_2$ is a hydrogen atom, a methyl group or a halogen atom directly from the corresponding furan-carbinols of the formula:

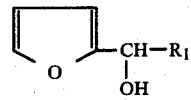

wherein $R_1$ is as defined above in a single step with an excellent yield, characterized in that the furan-carbinols are treated with water in the presence or absence of a catalyst.

4 Claims, No Drawings

PROCESS FOR PREPARING CYCLOPENTENOLONES

The present invention relates to a process for preparing cyclopentenolones. More particularly, it relates to a novel and improved process for preparing cyclopentenolones of the formula:

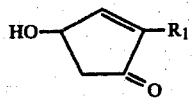     (I)

wherein $R_1$ is a straight, branched or cyclic alkyl group having not more than 6 carbon atoms (e.g. methyl, ethyl, propyl, hexyl, cyclopentyl, cyclohexyl), a straight, branched or cyclic alkenyl group having not more than 6 carbon atoms (e.g. allyl, 4-pentenyl, α-methylallyl, α-ethylallyl, 2-cyclopentenyl, 2-cyclohexenyl), a straight or branched alkynyl group having not more than 6 carbon atoms (e.g. propargyl) or a group of the formula:

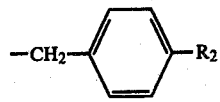

wherein $R_2$ is a hydrogen atom, a methyl group or a halogen atom (e.g. chlorine, bromine, fluorine).

The cyclopentenolones (I) are useful as the intermediates for the manufacture of agricultural chemicals, drugs, perfumes, etc. For their production, various methods are known, some of which are industrially adopted. But, they are still not satisfactory in respect of the yield, the complexity of operations, the problems of environmental pollution, etc. Among the known methods, there is included the one in which a furan-carbinol is used as the starting material [G. Piancatelli et al.: Tetrahedron, 35, 135 (1979); G. Piancatelli et al.: Tetrahedron Letters, 39, 3555 (1976)]. In this method, a 4-substituted-5-hydroxy-3-oxocyclopentene derivative is prepared in the following manner:

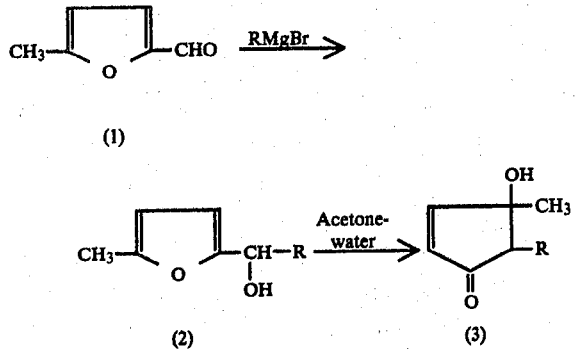

wherein R is phenyl, n-hexyl, methyl or t-butylheptanate. Piancatelli et al. also reported in said publication that the treatment of thus prepared compound (3) with neutral alumina provides the corresponding cyclopentenolone. However, in such case, the compounds (3) are obtained in a very low yield even after a prolonged reaction. Thus, it may be said that this method is impractical for production of the cyclopentenolones of the formula (I).

As the result of an extensive study, it has now been found that the cyclopentenolones of the formula (I) can be prepared directly from the furan-carbinols of the formula:

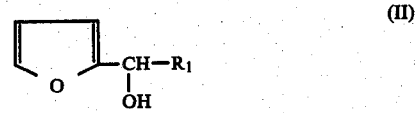     (II)

wherein $R_1$ is as defined above, by a one-step operation in a good yield. The present invention is based on the above finding.

According to the present invention, there is provided a process for preparing the cyclopentenolones (I) from the corresponding furan-carbinols (II), characterized in that the furan-carbinols (II) are treated with water to give directly the corresponding cyclopentenolones (I) in a single step.

The characteristic feature of the process of this invention resides in that the treatment is effected in water. Water may be used alone or contain a small proportion of any organic solvent (e.g. toluene, xylene, diisopropyl ether, benzene, acetone, tetrahydrofuran, dioxane). In this connection, it may be noted that the Piancatelli paper referred to above discloses that the treatment of the furan-carbinol (2) with acetone containing a small proportion of water in the presence of an acid affords the oxocyclopentene (3), but it is entirely silent on the production of the cyclopentenolone from the furan-carbinol (2).

In the process of this invention, the starting material is the furan-carbinol (II), which may be prepared by the reaction of furfural with a Grignard reagent of the formula: $R_1MX$ wherein $R_1$ is as defined above, M is Mg, Zn or $Al_{\frac{1}{3}}$ and X is a halogen atom.

On carrying out the process of the invention, it is desired that pH is maintained from 3 to 8 for accelerating the reaction rate and suppressing the proceeding of the side reaction, for instance, by the use of a basic and/or acidic substance as such or in solution.

In case of the pH being higher than the said upper limit, the reaction rate becomes markedly small or slow. In case of the pH being lower than the said lower limit, the side reaction proceeds so that the yield of the by-product is increased. The reaction temperature is usually within a range of 60° to 200° C., preferably within a range of 80° to 180° C. The introduction of a metal salt and/or a surfactant as a catalyst into the reaction system is effective in promoting the reaction rate and increasing the conversion.

As the basic or acidic substance to be used for regulation to the pH value or to be introduced intermediarily into the reaction system, any usual basic or acidic substance may be employed. Examples of the basic substance are hydroxides of alkali metals (e.g. sodium, potassium) and alkaline earth metals (e.g. calcium, barium), basic salts of said metals such as carbonates, bicarbonates and acetates, amines (e.g. triethylamine, pyridine), basic ion-exchange resins, etc. Examples of the acidic substance are inorganic acids (e.g. sulfuric acid, hydrochloric acid, nitric acid), organic acids (e.g. acetic acid, p-toluenesulfonic acid), acid metal salts (e.g. sodium dihydrogenphosphate, sodium hydrogensulfite), acid ion-exchange resins, etc. Buffer solutions containing these basic or acidic substances are also usable.

The amount of water to be used in the process of the invention may be usually from 0.5 to 200 parts by weight, preferably from 5 to 100 parts by weight, to 1 part by weight of the starting furan-carbinol (II).

Examples of the metal salt usable as the catalyst are magnesium chloride, magnesium bromide, magnesium sulfate, magnesium nitrate, manganese chloride, manganese nitrate, copper sulfate, cobalt acetate, zinc chloride, etc. The amount of the metal salt is usually from 0.001 to 100 mol, preferably from 0.01 to 10 mol, to 1 mol of the furan-carbinol (II). As the surfactant which serves as the catalyst, any of cationic and amphoionic ones may be employed. The amount of the surfactant is usually 0.1 to 20% by weight, preferably 1 to 5% by weight, to the furan-carbinol (II).

Practical and preferred embodiments of the present invention will be illustratively shown in the following Examples.

EXAMPLE 1

Dipotassium hydrogenphosphate (0.56 g) and potassium dihydrogenphosphate (1.77 g) were dissolved in water (400 ml) at 20° C. (pH 6.2). The buffer solution thus obtained and 2-furyl-allylcarbinol (5 g) were charged in an autoclave, heated with stirring up to 180° C. in 55 minutes and kept at this temperature for 4 hours (internal pressure, 9 kg/cm$^2$). After ice-cooling, the reaction mixture was admixed with sodium chloride (40 g) and extracted four times with methyl isobutyl ketone (100 ml). The extract was concentrated by distilling off methyl isobutyl ketone at 60° C. under reduced pressure to obtain an oily residue (4.5 g). The residue was purified by passing it through a column packed with silica gel (60 g) using a mixture of ethyl acetate and n-hexane (1:2 by volume) as an eluent. 2-Allyl-4-hydroxy-2-cyclopentenone was thus obtained with the yield of 4.1 g (82%).

IR$\nu_{C=O}$: 1710 cm$^{-1}$; IR$\nu_{C=C}$: 1650 cm$^{-1}$.

NMR (CDCl$_3$, 60 MHz): 7.32 (s, 1H, 3-H); 5.86 (complex m, 1H, —CH$_2$—C$\underline{H}$=CH$_a$H$_b$); 5.25 (m, 1H, —CH$_2$—CH=C$\underline{H}_a$H$_b$); 5.02 (m, 1H, —CH$_2$—CH=CH$_a$$\underline{H}_b$); 4.63 (broad d, 1H, 4-H); 4.28 (broad s, 1H, 4-OH); 2.98 (d, 2H, —C$\underline{H}_2$—CH=CH$_a$H$_b$); 2.69 (dd, 1H, 5-H); 2.42 (dd, 1H, 5-H).

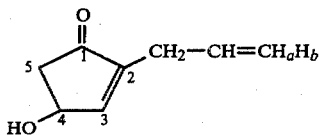

EXAMPLES 2 TO 4

In the same manner as described in Example 1, the cyclopentenolones (I) as shown in Table 1 were prepared under the conditions indicated in Table 1 using the furan-carbinols (II) (5 g).

TABLE 1

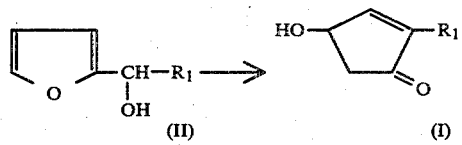

| Example No. | R$_1$ in starting material | Reaction time*[1] (hr) | Reaction temperature (°C.) | Reaction pressure (kg/cm$^2$) | Buffer Base (g) | Buffer Acid (g) | pH | Yield (%) |
|---|---|---|---|---|---|---|---|---|
| 2 | Propargyl | 4 | 180 | 9 | Sodium acetate (0.25) | Acetic*[2] acid | 5.8 | 71 |
| 3 | Cyclohexyl | 8 | 150 | 3.8 | Dipotassium hydrogenphosphate (0.56) | Potassium dihydrogenphosphate (1.77) | 6.2 | 76 |
| 4 | p-Chlorobenzyl | 4 | 180 | 9 | Sodium acetate (0.25) | Acetic*[2] acid | 5.8 | 82 |

Note:
*[1]Reaction time after the desired temperature was attained.
*[2]10% (v/v) aqueous acetic acid solution (0.2 ml).

EXAMPLE 5

Water (500 ml) and potassium dihydrogenphosphate (2.0 g) were placed in an autoclave, and the mixture was adjusted to pH 5.1 with an aqueous 1N NaOH solution at 30° C. α-Methylallyl-2-furylcarbinol (15 g) was then added, and the mixture was heated at 150° C. for 5.5 hours while stirring. After cooling, the reaction mixture was adjusted to pH 7.1 with an aqueous 1N NaOH solution at 30° C. and re-heated at 150° C. for 5 hours while stirring. After completion of the reaction, the mixture was admixed with sodium chloride (10 g) and extracted with methyl isobutyl ketone. The solvent was removed from the reaction mixture, and distillation of the resulting residue gave 2-(α-methylallyl)-4-hydroxy-2-cyclopentenone with the yield of 12 g (80%). B.P., 88°–90° C./0.12 mmHg.

EXAMPLES 6 TO 8

The cyclopentenolones (I) as shown in Table 2 were prepared as described in Example 5 using the furan-carbinols (II) (15 g) shown below:

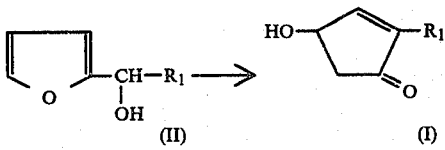

TABLE 2

| Example No. | R₁ in starting material (II) | Yield (%) | B.P. of product (I) |
| --- | --- | --- | --- |
| 6 | 2-Cyclopentenyl | 77 | 115–119° C./2 mmHg |
| 7 | α-Ethylallyl | 75 | 129–132° C./4 mmHg |
| 8 | α-Methylpropargyl | 65 | 125–131° C./3 mmHg |

EXAMPLE 9

A mixture of water (800 ml) and potassium dihydrogenphosphate (0.3 g) was heated to 100° C. and then adjusted to pH 5.0 with addition of phosphoric acid. 2-Furyl-2-cyclohexenylcarbinol (20 g) was then added, and the mixture was stirred under reflux for 20 hours while keeping the pH at 5.0. After addition of MgCl₂.6H₂O (20 g), the mixture was adjusted to pH 7.3 with an aqueous 1N NaOH solution and stirred for 8 hours under reflux. The reaction mixture was cooled, admixed with sodium chloride (20 g) and extracted with methyl isobutyl ketone. The extract was concentrated, and the residue was distilled to give 2-(2-cyclohexenyl)-4-hydroxy-2-cyclopentenone with the yield of 14.2 g (71%). B.P., 140°–145° C./1.5 mmHg.

EXAMPLE 10

Sodium acetate (0.25 g) and "Vionine D-4.8" (polyoxyethylene alkylphenyl ether manufactured by Takemoto Yushi Co., Ltd.; 0.44 g) were dissolved in water (200 ml), and the mixture was adjusted to pH 5.8 with addition of a 10% (v/v) aqueous acetic acid solution at 20° C.

The buffer solution thus obtained and 2-furylallylcarbinol (5 g) were charged in an autoclave, and the mixture was heated with stirring to 150° C. in 35 minutes and kept at this temperature for 8 hours while continuously stirring. The reaction mixture was ice-cooled, admixed with sodium chloride (40 g) and extracted four times with methyl isobutyl ketone (80 ml). The methyl isobutyl ketone was distilled off at 60° C. under reduced pressure to give an oily residue (4.6 g). The residue was purified by passing it through a column packed with silica gel (60 g) using a mixture of ethyl acetate and n-hexane (1:2 by volume) as an eluent. 2-Allyl-4-hydroxy-2-cyclopentenone was thus obtained with the yield of 4.2 g (84%).

EXAMPLE 11

Sodium acetate (0.25 g) and MgCl₂.6H₂O (0.27 g) were dissolved in water (200 ml), and the mixture was adjusted to pH 6.0 with addition of a 10% (v/v) aqueous acetic acid solution at 20° C.

The buffer solution thus obtained and 2-furylallylcarbinol (5 g) were charged in an autoclave, and the mixture was heated with stirring to 180° C. and kept at this temperature for 3.5 hours while stirring. The reaction mixture was ice-cooled, admixed with sodium chloride (40 g) and extracted with methyl isobutyl ketone. The extract was evaporated to give an oily residue (4.6 g). The residue was purified by passing it through a column packed with silica gel (60 g) using a mixture of ethyl acetate and n-hexane (1:2 by volume) as an eluent. 2-Allyl-4-hydroxy-2-cyclopentenone was thus obtained with the yield of 4.2 g (84%).

What is claimed is:

1. A one step process for preparing cyclopentenolones consisting essentially of treating a furan-carbinol of the formula:

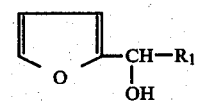

wherein R₁ is a straight, branched or cyclic alkyl group having not more than 6 carbon atoms, a straight, branched or cyclic alkenyl group having not more than 6 carbon atoms, a straight or branched alkynyl group having not more than 6 carbon atoms or a group of the formula:

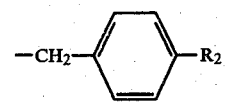

wherein R₂ is a hydrogen atom, a methyl group or a halogen atom in an aqueous medium in the presence or absence of a catalyst to obtain the corresponding cyclopentenolone of the formula:

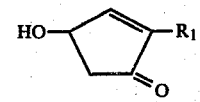

wherein R₁ is as defined above.

2. The process according to claim 1, wherein the reaction temperature is from 60° to 200° C.

3. The process according to claim 1 or 2, wherein the pH value of the aqueous medium is from 3 to 8.

4. The process according to claim 1, wherein the treatment is effected in the presence of a catalyst chosen from a metal salt and a surfactant.

* * * * *